United States Patent [19]

Igarashi et al.

[11] 4,248,865
[45] Feb. 3, 1981

[54] NOVEL AMINOGLYCOSIDE DERIVATIVES

[75] Inventors: Kikuo Igarashi, Itami; Tsunetoshi Honma, Ikoma, both of Japan

[73] Assignee: Shionogi & Co., Ltd., Osaka, Japan

[21] Appl. No.: 68,104

[22] Filed: Aug. 20, 1979

[30] Foreign Application Priority Data

Sep. 11, 1978 [JP] Japan .................. 53-112119

[51] Int. Cl.³ .................. A61K 31/71; C07H 15/22
[52] U.S. Cl. .................. 424/180; 536/4; 536/10; 536/17 R
[58] Field of Search ............. 536/17 R, 10; 424/180

[56] References Cited

U.S. PATENT DOCUMENTS

| | | | |
|---|---|---|---|
| 4,107,435 | 8/1978 | Ross | 536/17 |
| 4,166,114 | 8/1979 | Igarashi | 536/17 |

Primary Examiner—Johnnie R. Brown

Attorney, Agent, or Firm—Wenderoth, Lind & Ponack

[57] ABSTRACT

Novel aminoglycoside derivatives and their salts containing 2-deoxystreptamine moiety, of which the 1-amino group is modified with a group represented by the formula:

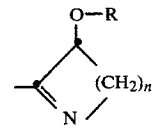

(wherein R is hydrogen or $C_1$ to $C_6$ alkanoyl; and n is an integer of 1 to 3.)

effective in treatment and prevention of infectious diseases caused by gram-positive and gram-negative bacteria.

11 Claims, No Drawings

NOVEL AMINOGLYCOSIDE DERIVATIVES

BACKGROUND OF THE INVENTION

Aminoglycoside antibiotics, for example, streptomycin, kanamycins, gentamicins, tobtamycin, etc. have practically been used as broad spectrum antimicrobials effective against gram-positive, gran-negative and acid-fast bacteria. The aminoglycoside antibiotics, however, are sometimes accompanied by undesired side effect such as nephropathy and deafness. Occurrence of resistant strains against the aminoglycosides is another problem to be solved. It has been attempted to modify such aminoglycoside with a specified group at the 1-amino group in order to improve the antimicrobial activity and relatively decrease the side effects. For instance, amikacin which is prepared by acylation of the 1-amino group of kanamycin A with (S)-4-amino-2-hydroxybutyric acid [Kawaguchi et al, J. Antibiotic, 25, 695 (1972); U.S. Pat. No. 3,781,268 (1973); J, Antibiotic 27, 677 (1974)] and butyrosin which is prepared by acylation of the 1-amino group of ribostamycin with (S)-4-amino-2-hydroxybutyric acid [U.S. Pat. No. 3,541,078] are well known. And besides, an aminoglycoside derivative which is prepared by introduction of (SR)-3-hydroxy-1-pyrrolin-2-yl into the 1-amino group of ribostamycin is published in Carbohydrate Research, 28 (1973), 263 to 280.

SUMMARY OF THE INVENTION

This invention relates to novel aminoglycoside derivatives having an excellent antimicrobial action.

The novel aminoglycoside antibiotic derivatives in this invention may be represented by the formula:

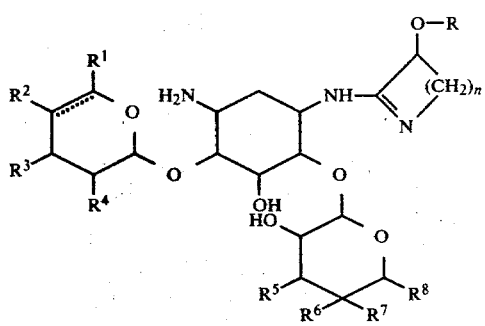

(wherein
R is hydrogen or $C_1$ to $C_6$ alkanoyl;
n is an integer of 1 to 3;
$R^1$ is aminomethyl, hydroxymethyl, 1-aminoethyl, or 1-methylaminoethyl;
$R^2$, $R^3$, and $R^6$ each is hydrogen or hydroxy;
$R^4$ is hydroxy or amino;
$R^5$ is amino or methylamino;
$R^7$ is hydroxy or methyl;
$R^8$ is hydrogen, hydroxymethyl or carbamoyloxymethyl;
and the dotted line represents the presence or absence of a double bond; provided that when the dotted line represents the presence of a double bond,
$R^5$ is methylamino.)

DETAILED EXPLANATION

In the aforementioned general formula (I), $C_1$ to $C_6$ alkanoyl means preferably $C_1$ to $C_4$ alkanoyl, e.g. formyl, acetyl, propionyl, butyryl, isobutyryl.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like and salts with organic acids such as acetic acid, fumaric acid, malic acid, tartaric acid, maleic acid, citric acid, mandelic acid, ascorbic acid, gallic acid, and the like.

Representatives of the compounds (I) are:
(1) 1-N-(3-hydroxy-1-azetin-2-yl)tobramycin
(2) 1-N-(3-hydroxy-1-pyrrolin-2-yl)tobramycin
(3) 1-N-(3-hydroxy-3,4,5,6-tetrahydropyridin-2-yl)tobramycin
(4) 1-N-(3-hydroxy-1-azetin-2-yl)kanamycin A
(5) 1-N-(3-hydroxy-1-pyrrolin-2-yl)kanamycin A
(6) 1-N-(3-hydroxy-3,4,5,6-tetrahydropyridin-2-yl)kanamycin A
(7) 1-N-(3-hydroxy-1-azetin-2-yl)gentamicin $C_1$
(8) 1-N-(3-hydroxy-1-pyrrolin-2-yl)gentamicin $C_1$
(9) 1-N-(3-hydroxy-3,4,5,6-tetrahydropyridin-2-yl)gentamicin $C_1$

PREPARATION

Compounds (I) may readily be prepared by reacting the well-known aminoglycosides of the formula:

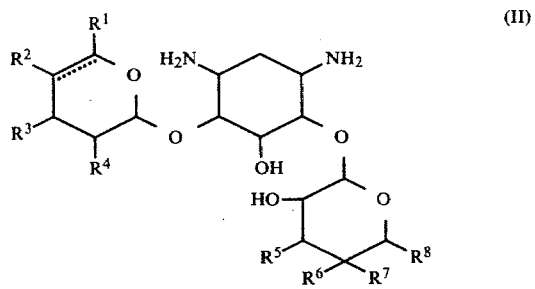

(wherein $R^1$, $R^2$, $R^3$, $R^4$, $R^5$, $R^6$, $R^7$, $R^8$, and the dotted line each has the same meaning as mentioned above.) with compounds of the formula:

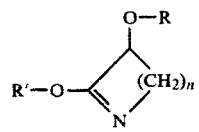

(wherein
R and n each has the same meaning as mentioned above; and
R' is lower alkyl).

The reaction is usually carried out in a suitable solvent in the presence of a proton source. In carrying out this reaction, an equimolar or excess amount of Compounds (III), preferably about 1.5 to 3 equivalents, is used to one mole of the aminoglycosides. The reaction proceeds well at room temperature and terminates within a period of 2 to 6 hours. If required, the reaction may be carried out at elevated temperatures for acceleration of the reaction. Examples of the solvents employed are alcohols such as methanol, ethanol, and ethylene glycol, dimethylsulfoxide, tetrahydrofuran, dioxane, and the like, and they may be used alone or as a mixture of two or more kinds of them. As proton sources, acids, preferably weak acids such as carboxylic acids, e.g. acetic acid are usually employed.

Since the Starting aminoglycosides (II) have many functional groups (e.g. amino group) other than the 1-amino group which readily react with Compounds (III), it is appropriate to optionally protect them by protecting groups before start of the reaction. Examples of the protecting groups are benzyloxycarbonyl of which the benzene ring may be substituted, formyl, t-butyloxycarbonyl, t-amyloxycarbonyl, methoxycarbonyl, ethoxycarbonyl, p-toluenesulfonyl, phthaloyl, m-nitrophenylthio, triphenylmethylthio and the like, and these protecting groups may be removed in conventional manners such as treatment with acids or catalytic hydrogenation after termination of the reaction.

When R of Compounds (III) is hydrogen, it is preferable to protect it with a suitable acyl group before the reaction.

Representative of the starting compounds (II) and their substituents are shown in Table 1.

Compounds (IV) are well-known and prepared, for example, in the manner as described in Tetrahedron Letters, 2617 (1971).

(1) Acylation

The acylation may be carried out by treating the Starting Compound (IV) with an equimolar or excess amount, preferably 1 to 2 equivalents of carboxylic acids or the reactive derivatives thereof corresponding to the acyl R in a suitable solvent in the presence or absence of a catalyst (e.g. pyridine, triethylamine).

The reaction proceeds enough at room temperature, but if required, it is possible to accelerate the reaction by warming at 30° to 70° C., preferably at 30° to 40° C. Examples of the reactive derivatives of carboxylic acids are acid halides, acid azides, acid anhydrides, active esters and the like. Examples of solvents to be used are ethers such as diethyl ether, 1,2-dimethoxyethane, tetrahydrofuran, and dioxane, methylene chloride, dimethylsulfoxide, pyridine, and the like, and they may be used alone or as a mixture of two or more kinds of them.

(2) Iminoetherification

This process may be carried out by treating the above

Table 1

| | $R^1$ | $R^2$ | $R^3$ | $R^4$ | $R^5$ | $R^6$ | $R^7$ | $R^8$ | double bond |
|---|---|---|---|---|---|---|---|---|---|
| tobramycin | $CH_2NH_2$ | OH | H | $NH_2$ | $NH_2$ | H | OH | $CH_2OH$ | none |
| kanamycin A | $CH_2NH_2$ | " | OH | OH | " | " | " | " | " |
| kanamycin B | $CH_2NH_2$ | " | " | $NH_2$ | " | " | " | " | " |
| kananycin C | $CH_2OH$ | " | " | " | " | " | " | " | " |
| deoxykanamycin A | $CH_2NH_2$ | " | H | OH | " | " | " | " | " |
| dideoxykanamycin B (dibekacin) | $CH_2NH_2$ | H | " | $NH_2$ | " | " | " | " | " |
| gentamicin $C_1$ | $CH(CH_3)NHCH_3$ | " | " | " | $NHCH_3$ | OH | $CH_3$ | H | " |
| gentamicin $C_2$ | $CH(CH_3)NH_2$ | " | " | " | " | " | " | " | " |
| gentamicin $C_{1a}$ | $CH_2NH_2$ | " | " | " | " | " | " | " | " |
| gentamicin B | $CH_2NH_2$ | OH | OH | OH | " | " | " | " | " |
| nebramycin factor 4 | $CH_2NH_2$ | " | " | $NH_2$ | $NH_2$ | H | OH | $CH_2OCONH_2$ | " |
| nebramycin factor 5' | $CH_2NH_2$ | " | H | " | " | " | " | " | " |
| sisomicin | $CH_2NH_2$ | H | " | " | $NHCH_3$ | OH | $CH_3$ | H | double bond |

Compounds (III) may be prepared as illustrated in the following reaction scheme:

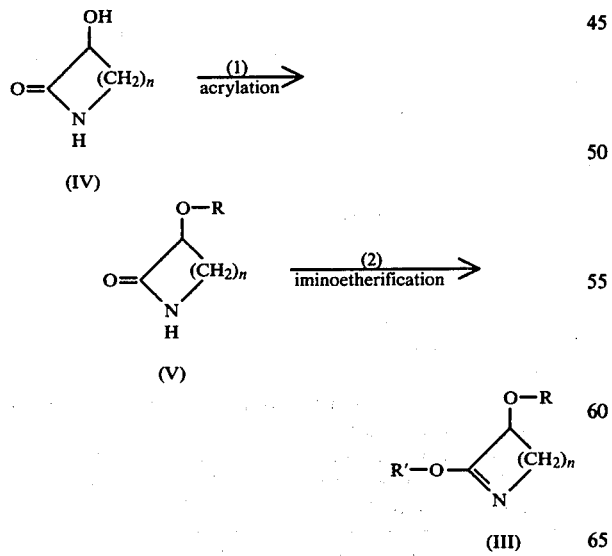

(wherein R, R' and n each has the same meaning as mentioned above.)

acylated intermediates (V) with an equimolar or excess amount, preferably 1 to 2 equivalents of etherifying agent corresponding to the alkyl to be introduced. Examples of etherifying agents are trialkyloxonium tetrafluoroborate, combined agents of silver oxide and alkyl halide, and the like.

The iminoetherification may also be achieved by reacting the starting compounds (IV) with a hydrohalogenic acid to the corresponding iminohalide, followed by reaction with a sodium alcoholate of the formula R'OHa.

EFFECT

The aminoglycoside antibiotic derivatives and the non-toxic salts thereof prepared in this invention exhibit excellent antimicrobial activities. They are several to several ten times more active than the corresponding parent aminoglycosides against some species of gram-positive and gram-negative bacteria. Minimum Inhibitory Concentration (MIC, µg/ml) of the modified aminoglycosides of this invention and the corresponding parent aminoglycosides is indicated in Table 2. MIC was determined by the following agar dilution method.

(1) Preparation of bacterial suspensions

One loopful of a strain of bacteria to be tested on agar slant was inoculated into a medium for growth of inoculum (Trypto Soy Broth; Eiken Chemical Co.) and incubated at 37° C. overnight.

(2) Preparation of medium for antibacterial activity test

A sample solution of aminoglycoside derivative was subjected to serial two-fold dilutions with sterile water. This diluted sample solutions were distributed to the Modified Mueller Hinton Agar medium (Nissui-seiyaku Co.), mixed gently and allowed to solidify.

(3) Determination of MIC values

One loopful of the bacterial suspension prepared in (1) was placed on the surface of the medium prepared in (2) containing the aminoglycoside derivative in various concentrations at $10^6$ CFU/ml inoculum size. After incubating at 37° C. for 18 to 20 hours, the growth of bacteria on the medium was observed according to the standard method of Japan Society of Chemotherapy.

Table 2

| Bacteria | MIC (μg/ml) Compound [A] | [B] | TOB |
|---|---|---|---|
| *Escherichia coli* W-677/JR 762* | 12.5 | 12.5 | 50 |
| *Klebsiella pneumoniae* K1-168* | 3.1 | 3.1 | 100 |
| *Proteus vulgaris* TB-615* | 25.0 | 25.0 | 50 |
| *Proteus mirabilis* TB-617 | 3.1 | 3.1 | 6.2 |
| *Pseudomonas aeruginosa* PP-6* | 3.1 | 6.2 | >100 |
| *Pseudomonas aeruginosa* TB-151* | 25.0 | 25.0 | 50.0 |

(Note)
[A] = 1-N-[(S)-(-)-3-hydroxy-1-pyrrolin-2-yl]tobramycin
[B] = 1-N-[(S)-(-)-3-hydroxy-3,4,5,6-tetrahydropyridin-2-yl]tobramycin
TOB = tobramycin
*represents tobramycin resistant strains.

As seen from Table 2, Compounds (I) of this invention are valuable antimicrobial agents effective against various species of the well-known aminoglycoside resistant strains (e.g. *Klebsiella pneumoniae, Pseudomonas aeruginosa*) as well as sensitive strains. Compounds (I) can also be used as disinfectants for preventing the growth of bacteria in perishable, feedstuffs, or hygenical materials.

HOW TO USE

Compounds (I) of this invention can be in a wide variety of oral or parenteral dosage forms solely or in admixture with other co-acting substances. The pharmaceutical compositions may be a mixture of 0.01 to 99% of Compounds (I) with a pharmaceutical carrier or carriers which can be a solid material or liquid material in which Compounds (I) are soluble, dispersible, or suspensible. They can be in a unit dosage form. The solid compositions can be in forms of tablets, powder, dry syrups, troches, granules, capsules, pills, suppositories, or like solid preparation. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricant (e.g. stearic acid, talc, paraffin, boric acid, silica, sodium benzoate, polyethylene glycol, cacao oil, magnesium sulfate); emulsifying agents (e.g. lecithin, sorbitan monooleate, acacia); suspending agents (e.g. sorbitol, methylcellulose, glucose, sugar syrup, gelatin, hydroxyethylcellulose, carboxymethylcellulose, aluminum stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on Compounds (I).

Compounds (I) of this invention, particularly, their sulfates, are readily soluble in water and conveniently used as solutions for intravenous, intramusclar, or subcutaneous injections according to a conventional method. Compounds (I) can be dissolved in an ampoule or oily solvent for injection to give an injectable solution in ampoule; in order to preserve the injectable preparation for a long period of time, it is appropriate to make a vial preparation containing crystals, powder, microcrystals, or lyophilizate of Compounds (I). The vial preparation may be dissolved or suspended in the said solvents for injection immediately before use. The preparation may contain said preservatives.

Further, Compounds (I) of this invention can be used as suppositories, ointments for topical or opthalmic use, powders for topical use, and like preparations preparable according to the methods well-known to those skilled in the art. The external preparation can contain 0.01 to 99% of Compounds (I) of this invention together with a necessary amount of pharmaceutical carrier given above.

This invention also provides a method for treating or preventing infections caused by bacteria in humans or domestic animals, which comprises administering to the humans or animals Compounds (I) of this invention at a divided or single dose of 0.01 to 5 g/kg a day for injection, 0.01 to 10 g/kg a day for oral administration, or 0.01 to 10 g a day for topical application at intervals of 3 to 12 hours.

The method is applicable for treating or preventing some infectious diseases caused by bacteria sensitive to the compounds of this invention, e.g. staphylodermia, anthropozoonosis, cystitis, pyelitis, pneumonia, pneumonitis, bronchitis, empyematic, naspharyngitis, tonsilitis, rhinitis, dermatitis, pustulosis, abscess, wound and soft tissue infections, ear infections, osteomyelitis, septicemia, enteritis, urinary tract infections, and pyelonephritis.

Preferably, Compounds (I) of this invention are given to a patient in forms of pharmaceutical preparation, e.g. powder, dry syrup, tablets, troches, granules, capsules, pills, suppositories, injections, ointments, dispersions, inhalant, suspensions, solutions, emulsions, syrups and elixirs. They may be in a unit dosage form e.g. tablets, troches, capsules, injections, vials, granules or powder in a separate container of package.

The following examples are provided to further illustrate this invention.

EXAMPLE 1

Preparation of (S)-(−)-3-acetoxy-2-ethoxy-1-pyrroline (1) To a solution of 1.439 g of (S)-(−)-3-hydroxy-2-pyrrolidinone [P. W. K. Woo, Tetrahedron Letters, 2617 (1971); mp. 103.5°–104.5° C., $[\alpha]_D^{26} = -118.8° \pm 2.3°$ (c=0.688, CHCl$_3$)] in 14 ml of pyridine is added 2.8 ml of acetic anhydride, and the mixture is allowed to stand at room temperature for 4 hours and concentrated under reduced pressure at a temperature below 40° C. The residue is crystallized from ether and recrystallized from methylene chloride-n-hexane to give 1.735 g of (S)-(−)-3-acetoxy-2-pyrrolidinone in 86.3% yield.

mp. 85.5°–87° C.

$[\alpha]_D^{26} = -40.1° \pm 0.8°$ (c=1.015, CHCl$_3$)

Elemental Analysis (for C$_6$H$_9$NO$_3$) Calcd (%): C, 50.35; H, 6.29; N, 9.79. Found (%): C, 50.50; H, 6.36; N, 9.66.

IR: $\nu_{max}^{Nujol}$ 3170, 3135, 1742, 1715, 1692 cm$^{-1}$.

(2) To a solution of 1.630 g (1.1 equivalents) of triethyloxonium tetrafluoroborate in 10 ml of dry methylene chloride is added a solution of 1.108 g of the above product dissolved in 12 ml of dry methylene chloride under nitrogen atmosphere, and the mixture is allowed to stand at room temperature overnight and cooled. A solution of 1.19 g of potassium carbonate in 1.2 ml of water is added thereto with stirring. The reaction mixture is washed with an ice-cooled aqueous sodium hydrogencarbonate solution, dried over magnesium sulfate, and evaporated to give 1.100 g of 3-acetoxy-2-ethoxy-1-pyrroline in 83% yield.

bp. 67.5° C./1.3 mmHg $[\alpha]_D^{26.5} -45.2° \pm 0.2°$ (c=2.41, CHCl$_3$)

Elemental Analysis (for C$_8$H$_{13}$NO$_3$.1/10H$_2$O) Calcd (%): C, 55.54; H, 7.69; N, 8.10. Found (%): C, 55.79; H, 7.75; N, 8.15.

IR: $\nu_{max}^{CHCl_3}$ 1737, 1653 cm$^{-1}$

EXAMPLE 2

Preparation of 1-N-[(S)-(−)-3-hydroxy-1-pyrrolin-2-yl]tobramycin (1) To a solution of 397 mg (2.32 mmoles; 2.4 equivalents) of (S)-(−)-3-acetoxy-2-ethoxy-1-pyrroline in 28 ml of methanol are added 573 mg (0.96 mmole) of 3,2′,6′,3″-tetra-N-formyltobramycin and two drops of acetic acid, and the mixture is refluxed for 5 hours, cooled, and concentrated under reduced pressure. The residue is treated with ether, and the resulting precipitate is collected by filtration, washed with ether, dissolved in methanol, and then reprecipitated with addition of ether. The collected precipitate (708 mg) is dissolved in 0.9 ml of water, mixed with 10 ml of concentrated hydrochloric acid-methanol (the volume ratio 22:109) and kept at 35.5° C. for 24 hours. The excess amount of hydrochloric acid is neutralized with Amberlite IR-45 (OH type) and the resin is filtered off. The filtrate is evaporated under reduced pressure to dryness to give 747 mg of 1-N-[(S)-(−)-3-hydroxy-1-pyrrolin-2-yl]tobramycin as the hydrochloride.

(2) A solution of 200 mg of the above product dissolved in 2 ml of water is adsorbed on a column of 10 ml of Amberlite IRA-400 (CH$_3$COOH type) and eluted with water. The eluate (20 ml) is evaporated under reduced pressure to give 234 mg of 1-N-[(S)-(−)-3-hydroxy-1-pyrrolin-2-yl]tobramycin as the acetate.

(3) A solution of 234 mg of the above product dissolved in 4 ml of water is adjusted at pH 1.7 with 14 ml of 0.1 N sulfuric acid and concentrated to 4 ml under reduced pressure. The residue is treated with 40 ml of ethanol and the resulting precipitate is collected by filtration, washed with ethanol, dissolved in water, treated with active carbon and lyophilized. The lyophilizate is allowed to stand until the weight becomes constant by absorption of moisture. Thus, 233 mg of 1-N-[(S)-(−)-3-hydroxy-1-pyrrolin-2-yl]tobramycin sulfate is obtained in 89% yield.

$[\alpha]_D^{26.0} +71.3° \pm 1.0°$ (c=1.060, H$_2$O)

Elemental Analysis (for C$_{22}$H$_{42}$N$_6$O$_{10}$.2.7H$_2$SO$_4$.11-H$_2$O) Calc (%): C, 26.07; H, 6.90; N, 8.29; S, 8.54. Found (%): C, 25.79; H, 6.66; N, 8.44; S, 8.57.

NMR: $\delta_{ppm}^{D_2O}$ 6.48d, 5.83d, 5.67(t, J=8.0 Hz).

EXAMPLE 3

Preparation of (S)-(−)-3-acetoxy-2-ethoxy-3,4,5,6-tetrahydropyridine (1) To a solution of 460 mg of (S)-(−)-3-hydroxy-2-piperidone [A. Hunter, Biochemical Journal, 35, 1298 (1941); mp. 170°–171° C., $[\alpha]_D^{26} = -3.0° \pm 0.1°$ (c=7.027, H$_2$O)] in 6 ml of pyridine is added 2 ml of acetic anhydride, and the mixture is allowed to stand at room temperature overnight and concentrated under reduced pressure. The residue is crystallized from ether and then recrystallized from ether to give 560 mg of (S)-(−)-3-acetoxy-2-piperidone as pillar crystals in 89% yield.

mp. 77°–78° C.

$[\alpha]_D^{26} = -20.5° \pm 0.2°$ (c=3.049, CHCl$_3$)

Elemental Analysis (for C$_7$H$_{11}$NO$_3$) Calcd(%): C, 53.49; H, 7.05; N, 8.91. Found(%): C, 53.28; H, 7.01; N, 8.79.

IR: $\nu_{max}^{Nujol}$ 3260, 1735, 1700, 1501 cm$^{-1}$.

(2) To a solution of 3.0 g of the above product dissolved in 20 ml of dry methylene chloride is added a solution of 3.99 g (1.1 equivalents) of triethyloxonium tetrafluoroborate in 40 ml of dry methylene chloride, and the mixture is allowed to stand at room temperature overnight, cooled, mixed with a solution of 2.692 g of potassium carbonate in 2.7 ml of water with stirring, washed with an ice-cooled aqueous sodium hydrogencarbonate solution, dried over magnesium sulfate, and evaporated. The resulting syrupy residue is further evaporated to dryness under reduced pressure to give 2.68 g of (S)-(−)-3-acetoxy-2-ethoxy-3,4,5,6-tetrahydropyridine in 76% yield.

bp. 67°14 67.5° C./1.3 mmHg $[\alpha]_D^{26.5} = -128.0° \pm 0.5°$ (c=3.123, CHCl$_3$)

Elemental Analysis (for C$_9$H$_{15}$NO$_3$.1/5 H$_2$O) Calcd(%): C, 57.24; H, 8.21; N, 7.42. Found(%): C, 57.47; H, 8.13; N, 7.42.

IR: $\nu_{max}^{CHCl_3}$ 1734, 1678 cm$^{-1}$.

EXAMPLE 4

Preparation of 1-N-[(S)-(−)-3-hydroxy-3,4,5,6-tetrahydropyridin-2-yl]tobramycin (1) To a solution of 204 mg (1.1 mmoles) of (S)-(−)-3-acetoxy-2-ethoxy-3,4,5,6-tetrahydropyridine in 16 ml of methanol are added 299 mg (0.5 mmole) of 3,2′,6′,3″-tetra-N-formyltobramycin and three drops of acetic acid, and the mixture is refluxed for 3 hours, cooled, concentrated under reduced pressure, and treated with ether. The resulting precipitate is collected by filtration, washed with ether, dissolved in methanol and reprecipitated with addition of ether. A solution of 385 mg of the precipitate in 0.8 ml of water is mixed with 5.41 ml of concentrated hydrochloric acid (volume ratio 22:109) and kept under warming at 33.5° C. for 24 hours. The excess amount of hydrochloric acid is neutralized with Amberlite IR-45 (OH type) and the resin is filtered off. The filtrate is evaporated under reduced pressure to give 410 mg of 1-N-[(S)-(−)-3-hydroxy-3,4,5,6-tetrahydropyridin-2-yl]tobramycin as the hydrochloride.

(2) A solution of 248 mg of the above product dissolved in 4 ml of water is adsorbed on a column of 10 ml of Amberlite IRA-400 ($CH_3COOH$ type) and eluted with water. The eluate is evaporated under reduced pressure to give 258 mg of 1-N-[(S)-(−)-3-hydroxy-3,4,5,6-tetrahydropyridin-2-yl]tobramycin as the acetate.

(3) To a solution of 258 mg of the above product dissolved in 5 ml of water is added 16.7 ml of 0.1 N sulfuric acid, and the mixture is concentrated to 2 ml under reduced pressure and treated with 20 ml of ethanol. The resulting precipitate is collected by filtration, washed with ethanol, dissolved in water, treated with active carbon and lyophilized. The lyophilizate is allowed to stand until the weight becomes constant with absorption of moisture. Thus, 311 mg of 1-N-[(S)-(−)-3-hydroxy-3,4,5,6-tetrahydropyridin-2-yl]tobramycin sulfate is obtained in 94% yield.

$[\alpha]_D^{27} = +67.2° \pm 1.0°$ (c=1.027, $H_2O$)

Elemental Analysis (for $C_{23}H_{44}N_6O_{10} \cdot 2.5H_2SO_4 \cdot 9.5H_2O$) Calcd(%): C, 28.16; H, 6.99; N, 8.57; S, 8.17. Found (%): C, 28.14; H, 6.93; N, 8.46; S, 8.06.

NMR: $\delta_{ppm}^{D2O}$ 6.45d, 5.78d, 5.08br.

We claim:

1. A member selected from the group consisting of (a) an aminoglycoside derivative represented by the formula:

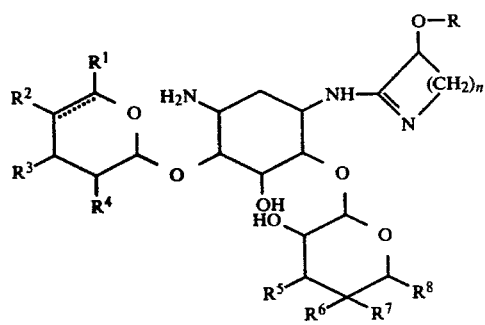

wherein

R is hydrogen or $C_1$ to $C_6$ alkanoyl;

n is an integer of 1 to 3;

$R^1$ is aminomethyl, hydroxymethyl, 1-aminoethyl, or 1-methylaminoethyl;

$R^2$, $R^3$ and $R^6$ each is hydrogen or hydroxy;

$R^4$ is hydroxy or amino;

$R^5$ is amino or methylamino;

$R^7$ is hydroxy or methyl;

$R^8$ is hydrogen, hydroxymethyl or carbamoyloxymethyl; and the dotted line represents the presence or absence of a double bond; provided that when the dotted line represents the presence of a double bond, $R^5$ is methylamino and provided further that $R^6$ and $R^7$ are not both hydroxy, and (b) a non-toxic acid addition salt thereof.

2. A compound claimed in claim 1, wherein n is an integer of 2 or 3.

3. A compound claimed in claim 1, wherein R is hydrogen.

4. A compound claimed in claim 1, wherein $R^8$ is hydrogen or hydroxymethyl.

5. A compound claimed in claim 1, wherein $R^1$ is aminomethyl or hydroxymethyl and $R^8$ is hydrogen or hydroxymethyl.

6. A compound claimed in claim 1, wherein $R^1$ is aminomethyl or hydroxymethyl and $R^8$ is hydroxymethyl.

7. A compound claimed in claim 1, wherein $R^1$ is aminomethyl, $R^2$ is hydroxy, $R^5$ is amino, $R^6$ is hydrogen, $R^7$ is hydroxy, and $R^8$ is hydroxymethyl.

8. A compound claimed in claim 1, namely 1-N-(3-hydroxy-1-pyrrolin-2-yl)tobramycin.

9. A compound claimed in claim 1, namely 1-N-(3-hydroxy-3,4,5,6-tetrahydropyridin-2-yl)tobramycin.

10. A composition which comprises a bactericidally effective amount of a compound or salt thereof according to claim 1 and a pharmaceutically acceptable carrier therefor.

11. A method for treating a bacterial infectious disease of humans or other species of animals which comprises administering to said human or other species of animal a bactericidally effective amount of a compound or salt thereof as defined in claim 1.

* * * * *